US00PP14395P29

(12) United States Plant Patent
Engelke et al.

(10) Patent No.: US PP14,395 P2
(45) Date of Patent: Dec. 23, 2003

(54) ROYAL ZOYSIAGRASS

(50) Latin Name: *Zoysia matrella L. Merr×Z. japonica Steud.*
Varietal Denomination: Royal

(75) Inventors: Milton Charles Engelke, Parker, TX (US); James Arnold Reinert, Plano, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 10/193,607

(22) Filed: Jul. 11, 2002

(51) Int. Cl.[7] ..... A01H 5/00
(52) U.S. Cl. ..... Plt./390
(58) Field of Search ..... Plt./390

*Primary Examiner*—Bruce R. Campell
*Assistant Examiner*—A Para
(74) *Attorney, Agent, or Firm*—Fulbright & Jaworski L.L.P.

(57) ABSTRACT

An asexually reproduced cultivar of perennial zoysiagrass that possess a unique combination of characteristics including purple anthers and white stigmas, an absence of leaf blade hairs, high turf quality and density, good shade tolerance, salinity tolerance, resistance to Rhizoctonia blight and zoysiagrass mite, moderate resistance to tropical sod webworm and hunting billbug, susceptibility to fall army worm and tawny mole cricket and a distinct DNA fingerprint.

3 Drawing Sheets

Botanical classification: *Zoyzia matrella×Zoysia japonica.*
Variety denomination: 'Royal'.

BACKGROUND OF THE INVENTION

This invention relates to a new and distinct perennial zoysiagrass cultivar identified as 'Royal zoysiagrass', referred to herein as 'Royal'. 'Royal' is the result of a natural open pollination of material clone TAES-2175 (e.g., K-151). The seedling progenies from the material line were vegetatively increased and tested in a replicated field trial at the Texas Agricultural Experiment Station, Texas A&M University, Dallas, Tex., beginning in 1985. In 1990, several exceptional entries were selected from among the trials, one of which was designated as DALZ9006, which was later named 'Royal'. The inventive variety exhibits a fine texture typical of *Z. matrella*-type clones such as 'Diamond' (U.S. Plant Pat. No. 10,636), 'Cavalier' (U.S. Plant Pat. No. 10,778) and 'Emerald' and is useful for home lawns, golf course fairways, tees, green surrounds, recreational sports areas or other applications that involve mowing heights from 1.0 to 5.0 cm.

For purposes of registration under the International Convention for the Protection of New Varieties of Plants ("UPOV") and noting Section 1612 of the Manual of Plant Examination Procedures, the new variety of zoysiagrass of the present invention is named 'Royal'.

BRIEF SUMMARY OF THE INVENTION

The present invention relates to a new and distinct asexually reproduced variety of perennial zoysiagrass between 1 to 3 years of age (*Zoysia matrella* (L.) Merr)×*Z. japonica* Steud.). The variety name is 'Royal zoysiagrass' and is characterized by its purple anthers, white stigmas, an absence of leaf blade hairs and high turf quality among other unique characteristics, all of which are maintained when propagated asexually.

The novel features which are believed to be characteristic of the invention together with further objects and advantages will be better understood from the following description when considered in connection with the accompanying figures.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

CHARACTERISTICS

'Royal' was characterized in greenhouse and field conditions and is a unique variety of zoysiagrass. Seeds collected from open pollinated maternal clones of the zoysiagrass germplasm nursery were planted, developed into plugs, and established in small field turf plots. 'Royal' demonstrated superior biotic and phenotypic characteristics and, thus, propagated by cuttings of stolons and rhizomes by rooting them in soil and expanding the rooted material to provide planting stock. The planting stock was observed for performance characteristics and for comparison of morphological characters after propagation. The inventive variety has been propagated by sod, plugs, sprigs and stolons. Seed reproduction with self-fertility is not common in the Zoysia spp. No seedling establishment from 'Royal' has been observed in either greenhouse or field studies.

'Royal' is distinguished from other varieties of zoysiagrass by a combination of characteristics including shade tolerance, salinity tolerance, turf quality, resistance to zoysiagrass mite and Rhizoctonia blight (brown patch) and moderate resistance to tropical sod webworm and hunting billbug. 'Royal' is closest in phenotypic appearance to the zoysiagrass variety 'Emerald' (unpatented). 'Royal' generally demonstrates fair-to-good winter hardiness. Further, the inventive variety grows at an intermediate to rapid rate, and exhibits an intermediate water use requirement. 'Royal' produces little thatch with an optimum mowing height of 1 to 5 mm. 'Royal' generally grows to cover a plot area within 10–12 months of establishment from 7 mm×10 mm plugs planted on 30 mm centers.

'Royal' spreads by both rhizome and stolon growth. The stolons have a mean internode length of 23.6 mm between the fourth and fifth nodes, with a mean internode width of 1.21 mm and node diameter of 1.53 mm (Table 1) (Reinert et al., 2002a). Stolons of 'Royal' root adventitiously at the nodes.

The internode stolon color of 'Royal' exposed to full sun is 5R 3/2 ; color notations of plant tissues were based on the Munsell Color Charts for Plant Tissues, Munsell Color, Baltimore, Md., 1977. One of ordinary skill in the art recognizes that color notations are affected by light quality, photoperiod, and general growth of the plant. Measured in full-sun under field conditions in August, 2000, the genetic, adaxial leaf color of 'Royal' is 2.5G 4/4 to 2.5G 5/2 as compared to 'El Toro' (U.S. Plant Pat No. 5,845), which has a leaf color of 2.5 G 5/2 , and 'Meyer' (unpatented), which has a color of 2.5 G 4/2 (Munsell, 1977).

Figure 1:
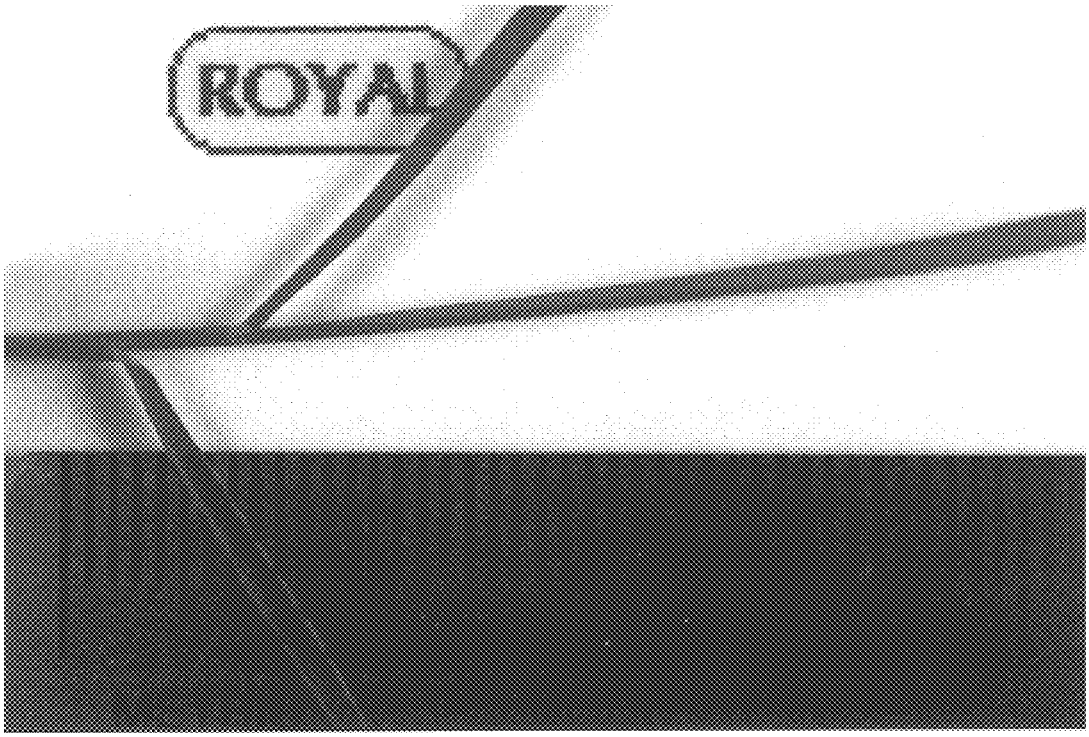
FIG. 1 is a photograph of the leaf blade and ligule of 'Royal'.

The ligule of 'Royal' is a row of silky hairs, achieving approximately 1 mm in maximum length. The ligule is illustrated in FIG. 1.

Leaf blades of 'Royal' are rolled in the bud, and are flat and stiff. Measurements of the third youngest leaf included a width of 1.36 mm and a length of 8.2 mm (Table 2) (Reinert et al., 2002a), which is significantly narrower and shorter than 'Meyer', 'Crowne' and 'El Toro' varieties. The abaxial/adaxial leaf surfaces lack hairs. Leaf blades are illustrated in FIG. 1.

Figure 2:
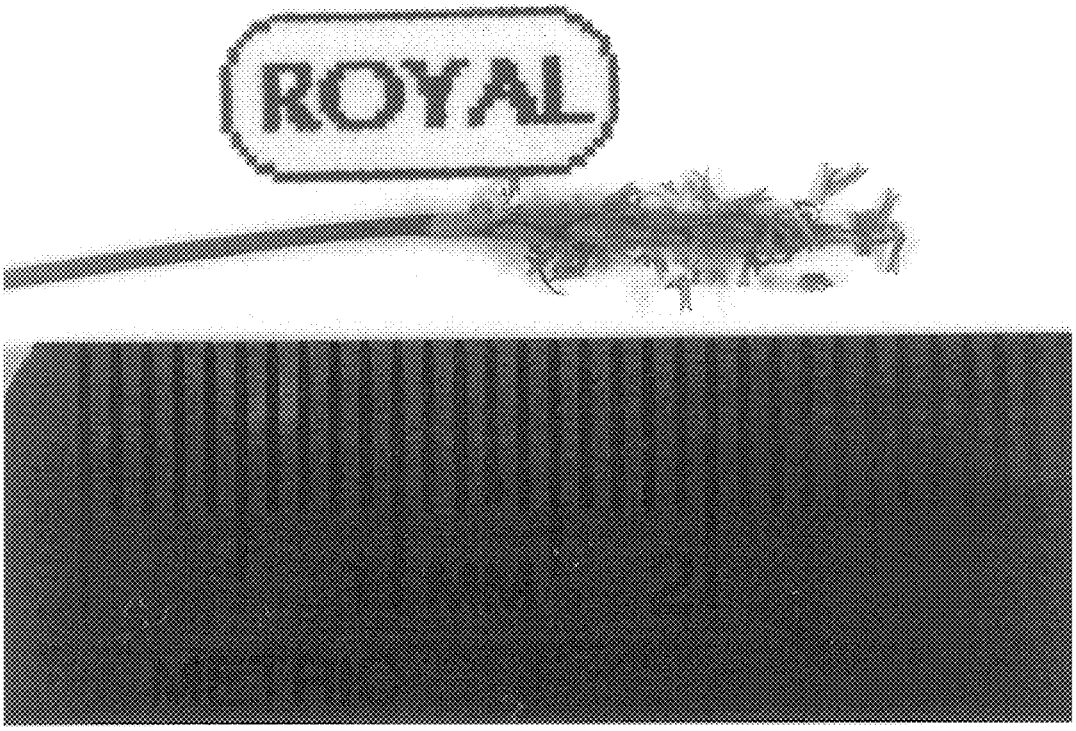
FIG. 2 is a photograph of the inflorescence of 'Royal'.

Measured under greenhouse conditions at Dallas,Tex., January 1996, the flag leaf of 'Royal' has a mean length of 5.24 mm. 'Royal' has purple anthers and white colored stigmas, undistinguishable in shade of color. The inflorescence is a terminal spike-like raceme, with spikelets on short pedicels (see FIG. 2). 'Royal' has a mean culm length of 6.7 cm, and an inflorescence length of 22.9 mm with a mean of 27.6 florets per raceme. The raceme is longer than 'Diamond' and more similar in length to 'Crowne'.

The somatic chromosome number in 'Royal' is 40.

'Royal' was entered in the National Turfgrass Evaluation Program, National Zoysiagrass Test-1991 (NTEP-1991) and was evaluated alongside 23 other zoysiagrass genotypes at 22 different geographic locations covering 17 states in the United States. The evaluation period lasted 4 years (1992–1995). In the NTEP-1991 test for the years 1992–1995, 'Royal' ranked ninth for the last two years and ninth overall in quality among the zoysiagrass genotypes tested (Table 3) (Morris, 1995b). Further, 'Royal' had the best density rating among the entries over the 4-yr evaluation period (Table 4) (Morris, 1993; Morris, 1994a; Morris, 1994b; and Morris 1995a).

The Turf Performance Index (TPI) is based on the number of times an entry occurred in the top statistical group, ranked 'Royal' in the top grouping 25 times as compared to 'Cavalier' (24 top groupings), 'Emerald' (23 top groupings) and 'Diamond' (22 top groupings). In contrast, the commercial standard varieties, 'Meyer' and 'El Toro', ranked in the top statistical grouping only 13 and 11 times, respectively. In studies in Griffin, Ga., 'Royal' was ranked among the densest turfs having good genetic color (Carrow, 1991; Carrow, 1992).

In the NTEP-1991 evaluation, 'Royal ' exhibited good shade tolerance as compared to the other zoysiagrasses. Each genotype was planted and evaluated in a shaded site (ca. 90%) under live-oak trees (*Quercus virginiana* Mill.) in Dallas, Tex., on September 1992 (Table 5) (Yamamato and Engelke, 1996). Turf performance characteristics evaluated at the shaded site included; turf quality, turf cover, green cover, color, density and texture. Turf cover was evaluated as a percentage of plot area covered with turf, and the TPI was used to evaluate overall turf quality. In general, the varieties took nearly 9 months to spread and cover at least 50% of the plot area. Thereafter, the 'Royal', 'Crowne', 'Emerald', 'Zorro' and 'Diamond' varieties increased turf cover to greater than 80%. 'Royal' ranked fifth behind 'Diamond', 'Zorro' and 'Crowne' among the 25 entries in the trial.

STRESS RESISTANCE

The inventive variety exhibits excellent salt tolerance. Under greenhouse conditions in hydroponics tanks, the salinity was gradually increased from zero to 400 mM NaCl. 'Royal' sustained a 33.6% leaf-firing injury, which was similar to 'El Toro', 'Emerald' and 'Cavalier' and significantly less than 'Meyer', which sustained 54.3% damage (Marcum et al., 1998).

'Royal' is resistant to Rhizoctonia blight and zoysiagrass mite and moderately resistant to tropical sod webworm and hunting billbug. Rhizoctonia blight (brown patch) is caused by the fungal pathogen *Rhizoctonia solani* Kühn. 'Meyer' and 'Royal' (10.8 and 15.8% disease infection, respectively) were among the most resistant to the fungus over a 7-day evaluation period when 24 zoysiagrass genotypes were inoculated under ideal disease conditions with the fungal pathogen in a growth chamber at Dallas, Tex. (Table 7) (Metz et al., 1994).

'Royal' is resistant to the zoysiagrass mite *Eriophyes zoysiae* Baker, Kono and O'Neill as compared to 'Meyer', 'Belair' (unpatented) and many other zoysiagrass genotypes which are very susceptible to the mite (Table 8) (Reinert et al., 1993). This mite has been identified in Maryland, Florida, Texas and other zones of extensive use of zoysiagrass. Under heavy infestation pressure in greenhouse conditions, a mean of 0.2 infested leaves per 5×5 cm plant was observed in the inventive variety. In comparison, 'Diamond', 'Cavalier', 'Belair' and 'Meyer' each exhibited greater than 9.4 infested leaves per plant.

The inventive variety is susceptible to fall armyworm (*Spodoptera frugiperda* J. E. Smith) larvae (Reinert and Engelke, unpublished data) and tawny mole cricket (*Scapteriscus vicinus* Scudder) (Braman et al., 1994).

'Royal' is moderately resistant to feeding by tropical sod webworm (*Herpetogramma phaeopteralis* Guenée) larvae. The visual rating was 4.6 for the inventive variety as compared to the 1.4 visual rating of 'Meyer' (Table 9) (Reinert and Engelke, 2001). The visual rating is determined on a scale of 1–9, with 1=near complete defoliation. Larvae that developed on 'Royal' weighed 15.1 mg after 15 days of feeding, which was larger than the 7.2 mg larvae that developed on the most resistant 'Cavalier', and one-half the size of larvae that developed on 'Meyer' (36.4 mg) (Table 10). Additionally, larvae on 'Royal' required 4.4 days longer to develop to adult emergence.

'Royal' is moderately resistant to the hunting billbug (*Sphenophorus venatus vestitus* (Chittenden)) in a cage study with eight other zoysiagrasses in Dallas, Tex. (Table 11) (Reinert et al., 2002b). Compared to 'Meyer' and 'Palisades', which exhibited 44.4 and 45.5% leaf-firing damage of the plant canopy, respectively, 'Royal' expressed 20.95% leaf-firing damage. Evaluation of whole plant growth potential (dry weight) indicated that 'Royal' sustained a 53.46% reduction as compared to a 70.2%, a 73.9% and a 73.9% reduction for 'El Toro', 'Meyer' and 'Palisades', respectively. The lower the reduction the greater expression of natural plant resistance.

DNA FINGERPRINTING

Figure 3:
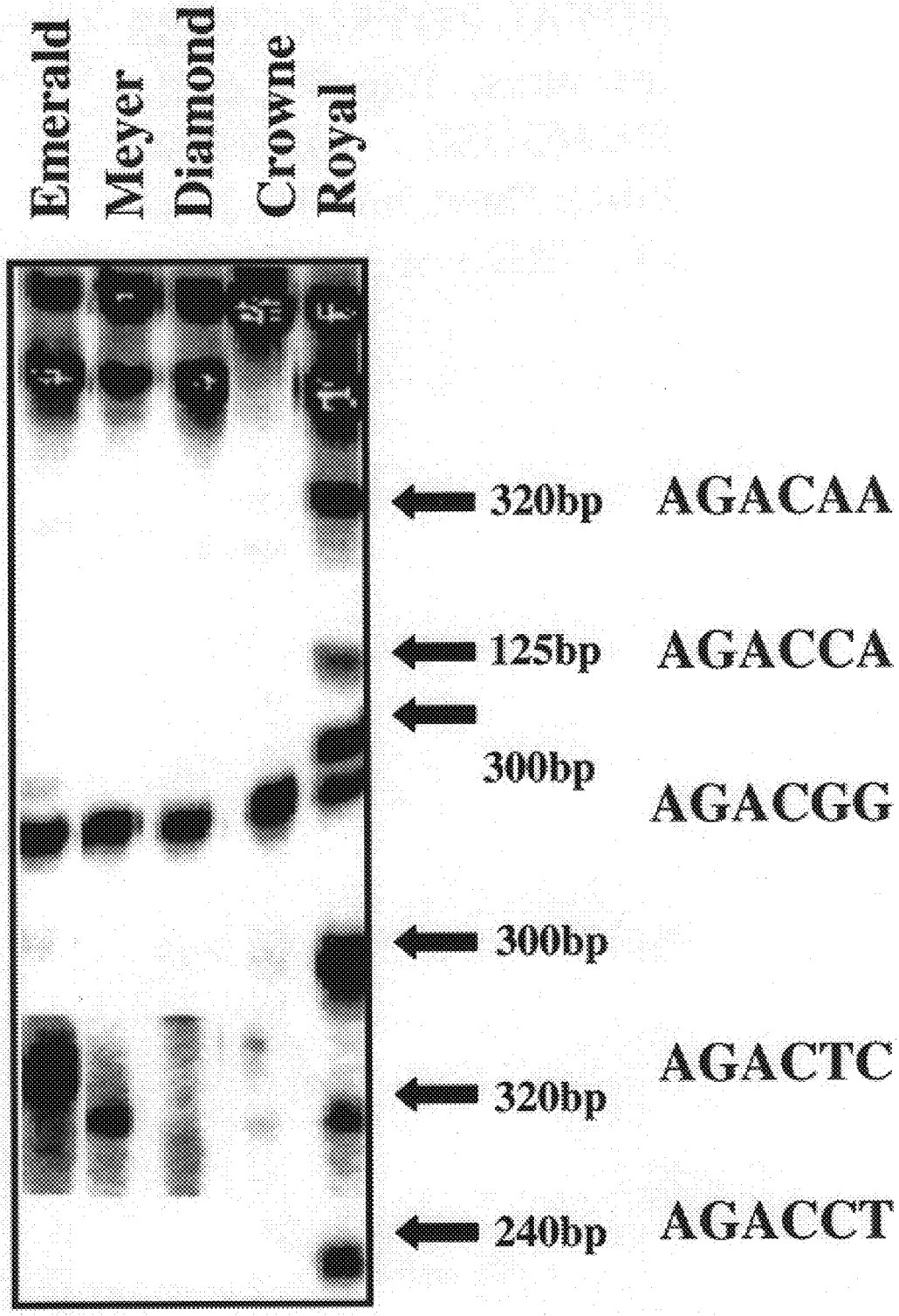
FIG. 3 is a DNA fingerprint of 'Royal' as compared to zoysiagrass varieties 'Meyer', 'Emerald', 'Crowne' and 'Diamond'.

Molecular markers have been used widely and successfully for genotyping varieties and species. Amplified Fragment Length Polymorphism (AFLP) is one such highly informative marker assay to generate fingerprints of simple and complex species and cultivars. The fingerprints generated for the identification of the cultivar 'Royal' as compared to cultivars 'Emerald', 'Meyer', 'Diamond' and 'Crowne' used sixty AFLP primer combinations. Of which, the primer combinations that provided the greatest separation included P-AGA/ M-CAA, P-AGA/ M-CCA, P-AGA/ M-CGT and P-AGA/ M-CTC. The latter primer combination, P-AGA/ M-CCT, allowed amplification of signature bands at 320, 300, 300, 320 and 240 base pair lengths (FIG. 3). These signature bands are useful to identify and differentiate 'Royal' cultivar from other varieties tested.

TABLE 1

Rhizome internode length as measured between the fourth and fifth nodes, internode diameter of the fourth internode, and node diameter of the fourth node of nine Zoysia cultivars. Plants grown in sand beds in the field under irrigation during the summer from June to September 2000, Dallas, TX.

| Cultivar | Internode length (mm) | Internode diameter (mm) | Node diameter (mm) |
|---|---|---|---|
| El Toro | 43.6 a[1] | 1.71 a | 2.63 a |
| Palisades | 40.0 ab | 1.55 ab | 2.48 a |
| De Anza | 34.5 bc | 1.39 bc | 1.93 cd |
| Crowne | 31.7 cd | 1.56 ab | 2.36 ab |
| Cavalier | 28.8 cd | 1.38 bc | 1.88 ed |
| Zorro | 27.0 cd | 1.25 c | 1.76 de |
| Meyer | 26.5 cde | 1.54 ab | 2.16 bc |
| Royal | 23.6 de | 1.21 c | 1.53 e |
| Diamond | 18.4 e | 1.19 c | 1.56 e |
| LSD | 8.1 | 0.22 | 0.31 |

[1]Mean in a column followed by the same letter are not significantly different by Fisher's protected LSD (P = 0.01).
Data taken from Reinert et al., 2002a.

TABLE 2

Leaf blade width and length measured on the third youngest leaf of nine Zoysia cultivars. Plants were grown in sand beds in the field under irrigation during the summer from June to September 2000, Dallas, TX.

| Cultivar | Blade width (mm) | Blade length (mm) |
|---|---|---|
| El Toro | 3.51 ab[1] | 10.8 abc |
| Palisades | 3.16 b | 8.5 bcd |
| De Anza | 1.73 c | 6.7 de |
| Crowne | 3.46 ab | 11.1 ab |
| Cavalier | 1.58 c | 10.0 abc |
| Zorro | 1.35 cd | 10.9 ab |
| Meyer | 3.54 a | 12.2 a |
| Royal | 1.36 cd | 8.2 cd |
| Diamond | 1.09 d | 4.4 e |
| LSD | 0.39 | 2.7 |

[1]Mean in a column followed by the same letter(s) are not significantly different by Fisher's protected LSD (P = 0.01).

TABLE 3

Mean turfgrass quality ratings of 24 zoysiagrass cultivars grown in the National Turfgrass Evaluation Program; National Zoysiagrass Test-1991 at 22 locations in the United States (1992–1995). Turfgrass quality ratings 1–9; 9 ideal turf[1]

| Variety | Overall mean 1992 | Overall mean 1993 | Overall mean 1994 | Overall mean 1995 | Overall mean 1992–95 | Mean ranking 1992–95 |
|---|---|---|---|---|---|---|
| Cavalier | 5.95 | 6.23 | 5.89 | 5.99 | 5.93 | 1 |
| TC 2033 | 5.85 | 6.10 | 6.11 | 5.96 | 5.91 | 2 |
| Sunburst | 5.83 | 5.91 | 5.81 | 5.87 | 5.85 | 3 |
| TC 5018 | 5.80 | 5.81 | 5.92 | 5.70 | 5.81 | 4 |
| Emerald | 5.74 | 6.21 | 6.05 | 5.73 | 5.79 | 5 |
| Omni | 5.56 | 6.13 | 6.06 | 5.69 | 5.73 | 6 |
| QT 2004 | 5.56 | 6.01 | 5.86 | 5.57 | 5.63 | 7 |
| DALZ8508 | 5.59 | 6.06 | 5.74 | 5.60 | 5.60 | 8 |
| Royal | 5.65 | 6.05 | 5.59 | 5.54 | 5.59 | 9 |
| Palisades | 5.82 | 5.82 | 5.46 | 5.44 | 5.59 | 9 |
| Crowne | 5.80 | 5.76 | 5.50 | 5.45 | 5.55 | 11 |
| El Toro | 5.78 | 5.63 | 5.34 | 5.41 | 5.50 | 12 |
| CD 259-13 | 5.30 | 5.53 | 5.74 | 5.49 | 5.40 | 13 |
| Meyer | 5.26 | 5.70 | 5.76 | 5.47 | 5.39 | 14 |
| QT 2047 | 5.37 | 5.39 | 5.26 | 5.16 | 5.30 | 15 |
| Belair | 4.99 | 5.58 | 5.61 | 5.02 | 5.16 | 16 |
| DALZ8516 | 4.72 | 5.42 | 4.96 | 5.05 | 4.86 | 17 |
| Diamond | 4.40 | 5.03 | 4.58 | 4.36 | 4.41 | 18 |
| DALZ8501 | 4.88 | 4.31 | 3.99 | 4.05 | 4.27 | 19 |
| DALZ8701 | 4.23 | 4.10 | 3.71 | 3.58 | 3.85 | 20 |
| LSD | 0.22 | 0.2 | 0.2 | 0.2 | 0.17 | |

[1]To determine statistical differences among entries, subtract one entry's mean from another entry's mean. Statistical differences occur when this value is larger than the corresponding LSD value (P = 0.05).
Data taken from Morris, 1995b.

TABLE 4

Turf performance index for density ratings of the National Turfgrass Evaluation Program; National Zoysiagrass Test-1991 summarized by season for the 4-yr period (1992–1995).

| | Turf Performance Index[1] | | | |
|---|---|---|---|---|
| Genotype | Spring | Summer | Fall | Total |
| Royal | 6 | 10 | 9 | 25 |
| Cavalier | 5 | 10 | 9 | 24 |
| Emerald | 7 | 7 | 9 | 23 |
| DALZ8508 | 5 | 9 | 9 | 23 |
| Diamond | 5 | 9 | 8 | 22 |
| Marquis | 5 | 8 | 9 | 22 |
| QT 2004 | 5 | 8 | 7 | 20 |
| DALZ8516 | 3 | 8 | 8 | 19 |
| Omni | 3 | 7 | 8 | 18 |
| DALZ8501 | 2 | 4 | 7 | 13 |
| Meyer | 4 | 5 | 4 | 13 |
| TC 5018 | 3 | 4 | 5 | 12 |
| Sunburst | 3 | 5 | 4 | 12 |
| CD259-13 | 4 | 4 | 4 | 12 |
| Palisades | 3 | 4 | 4 | 11 |
| El Toro | 2 | 4 | 5 | 11 |
| Belair | 3 | 3 | 4 | 10 |
| QT 2047 | 3 | 3 | 3 | 9 |
| Crowne | 3 | 3 | 3 | 9 |
| DALZ8701 | 0 | 3 | 3 | 6 |
| TGS-W10 | 1 | 2 | 2 | 5 |
| JZ-1 | 0 | 3 | 2 | 5 |
| TGS-B10 | 0 | 2 | 1 | 3 |
| Korean Common | 0 | 2 | 1 | 3 |

[1]Turf Performance Index is the number of times an entry was rated in the top statistical group.
Data taken from Morris, 1993; Morris, 1994a; Morris, 1994b; and Morris 1995a

TABLE 5

Turf Performance Index and percent ground cover for the National Turfgrass Evaluation Program; National Zoysiagrass Test-1991 planted under 90% shade at Dallas, TX (1992–1995).

| Entry | TPI[1] | % plot cover | Rank |
|---|---|---|---|
| Diamond | 46 | 93.9 | 1 |
| DALZ8516 | 46 | 93.9 | 1 |
| DALZ8508 | 42 | 85.7 | 3 |
| Zorro[2] | 41 | 83.7 | 4 |
| Crowne | 40 | 81.6 | 5 |
| Royal | 40 | 81.6 | 5 |
| 'Emerald | 40 | 81.6 | 5 |
| TC2033 | 40 | 81.6 | 5 |
| Palisades | 38 | 77.6 | 9 |
| Cavalier | 36 | 73.5 | 10 |
| El Toro | 32 | 65.0 | 11 |
| DALZ8701 | 29 | 59.1 | 12 |
| CD2013 | 25 | 51.0 | 13 |
| TGS-W10[3] | 25 | 51.0 | 13 |
| DALZ8501 | 24 | 49.0 | 15 |
| Sunburst | 23 | 46.9 | 16 |
| TC5018 | 22 | 44.9 | 17 |
| ITR90-3 | 19 | 38.8 | 18 |
| Korean Common[3] | 17 | 34.7 | 19 |
| Belair | 16 | 32.6 | 21 |
| Meyer | 16 | 32.6 | 21 |
| TGS-B10[3] | 16 | 32.6 | 21 |
| QT2047 | 15 | 30.6 | 23 |
| JZ-1#A89[3] | 13 | 26.5 | 24 |
| CD259-13 | 11 | 22.4 | 25 |
| QT2004 | 10 | 20.4 | 26 |

[1]Turf Performance Index is the number of times an entry was rated in the top statistical group Maximum number of observations = 49.
[2]Evaluated as DALZ9006.
[3]Seeded entry.
Data taken from Yamamoto and Engelke, 1996.

TABLE 6

Salinity tolerance of 59 zoysiagrass genotypes in greenhouse Hoagland's solutions (mean percent salt injury to shoots for 20 rating dates) tested at Dallas, TX.

| Genotype | Zoysia spp.[1] | Mean % injury |
|---|---|---|
| P9 | *Z. matrella* | 32 a[2] |
| Diamond | *Z. matrella* | 33 ab |
| DALZ8501 | *Z. matrella* | 33 ab |
| T38 | *Z. matrella* | 33 ab |
| T16 | *Z. macrostaychya* | 33 ab |
| T14 | *Z. macrostaychya* | 33 ab |
| P47 | *Z. matrella* | 33 abc |
| P2 | *Z. matrella* | 33 abc |
| DALZ8701 | *Z. matrella* | 35 a–d |
| DALZ8508 | *Z. matrella* | 37 a–e |
| P58 | *Z. sinica* | 37 a–e |
| P49 | *Z. sinica* | 37 a–e |
| El Toro | *Z. japonica* | 38 a–e |
| J239 | *Z. japonica* | 38 a–e |
| P50 | *Z. sinica* | 39 a–f |
| T4 | *Z. sinica* | 40 a–g |
| Royal | *Z. matrella* | 41 a–h |
| K227 | *Z. matrella* | 41 a–h |
| K12 | *Z. matrella* | 41 a–h |
| K245 | *Z. japonica* | 41 a–h |
| Emerald | *Z. matrella x Z. pacifica* | 41 a–h |
| Cavalier | *Z. matrella* | 42 a–h |
| TC2033 | *Z. matrella* | 42 a–h |
| K103 | *Z. korenia* | 42 a–h |
| QT2047 | *Z. japonica* | 42 a–h |
| K260 | *Z. korenia* | 43 a–i |
| K98 | *Z. korenia* | 43 b–i |
| J207 | *Z. tenuifolia* | 43 b–i |

TABLE 6-continued

Salinity tolerance of 59 zoysiagrass genotypes in greenhouse Hoagland's solutions (mean percent salt injury to shoots for 20 rating dates) tested at Dallas, TX.

| Genotype | Zoysia spp.[1] | Mean % injury |
|---|---|---|
| T44 | *Z. sinica* | 45 c–i |
| J222 | *Z. matrella* | 45 d–j |
| K99 | *Z. korenia* | 46 e–j |
| T21 | *Z. macrostaychya* | 46 e–k |
| Crowne | *Z. japonica* | 46 ek[2] |
| Palisades | *Z. japonica* | 46 e–k |
| J225 | *Z. matrella* | 47 e–k |
| K246 | *Z. macrostaychya* | 49 f–k |
| J3-2 | *Z. japonica* | 49 f–k |
| Belair | *Z. japonica* | 50 f–k |
| DALZ8516 | *Z. japonica* | 50 g–m |
| Sunburst | *Z. japonica* | 52 h–m |
| QT2004 | *Z. matrella* | 54 i–m |
| J87-2 | *Z. japonica* | 56 j–n |
| ITR90-3 | *Z. japonica* | 56 j–n |
| K248 | *Z. macrostaychya* | 57 j–n |
| TC5018 | *Z. japonica* | 57 k–n |
| Meyer | *Z. japonica* | 58 l–n |
| CD2013 | *Z. matrella* | 59 l–n |
| CD259-13 | *Z. japonica* | 60 l–o |
| K254 | *Z. matrella* | 61 m–o |
| JS10-3 | *Z. japonica* | 66 n–p |
| TGS-W10 | *Z. japonica* | 66 n–p |
| K241 | *Z. japonica* | 71 o–q |
| JS23 | *Z. japonica* | 73 pq |
| J94-5 | *Z. japonica* | 73 pq |
| TGS-B10 | *Z. japonica* | 73 pq |
| K157 | *Z. japonica* | 74 pq |
| Korean Common | *Z. japonica* | 76 pq |
| JZ-1 | *Z. japonica* | 79 q |
| K162 | *Z. japonica* | 81 q |

[1]Species identity is sometimes an estimate.
[2]Means with the same letter are not significantly different by Waller-Duncan k-ratio t test (k- = 100) (P = 0.05).
Data taken from Marcum et al., 1994.

TABLE 7

Resistance to Rhizoctonia blight (caused by *Rhizoctonia solani*) among zoysiagrasses in a laboratory study, Dallas. TX.

| Cultivar | Textural class[1] | Mean % infection[2] | Mean recovery[3] |
|---|---|---|---|
| CD2013 | 3 | 100.0 a[4] | 1.0 a |
| Korean common | 4 | 77.8 b | 1.9 b |
| Crown | 4 | 76.7 b | 2.0 bc |
| DALZ8701 | 3 | 73.0 bc | 2.5 def |
| Sunburst | 4 | 70.0 bcd | 2.3 cde |
| Belair | 4 | 67.5 bcd | 1.3 a |
| GT2047 | 4 | 64.2 bcd | 2.2 bcd |
| JZ1A89-1 | 3 | 60.8 cd | 1.3 a |
| GT2004 | 3 | 57.5 cde | 2.2 bcd |
| DALZ8501 | 1 | 55.8 def | 2.3 cde |
| CD259-13 | 4 | 53.3 d–g | 2.2 bcd |
| TC5018 | 4 | 42.5 e–h | 2.3 cde |
| TGS-W10 | 4 | 38.3 e–h | 2.2 bcd |
| El Toro | 4 | 37.5 ghi | 2.7 efg |
| Emerald | 3 | 36.2 ghi | 2.3 cde |
| Palisades | 4 | 35.0 hi | 2.5 def |
| TGS-B10 | 4 | 34.2 hi | 2.0 bc |
| DALZ8508 | 2 | 32.5 hij | 2.8 fg |
| DALZ8516 | 2 | 30.0 hij | 2.8 fg |
| TC2033 | 3 | 29.2 hij | 2.7 efg |
| Diamond | 1 | 26.7 h-k | 3.0 g |
| Cavalier | 3 | 20.0 ijk | 2.3 cde |

TABLE 7-continued

Resistance to Rhizoctonia blight (caused by *Rhizoctonia solani*) among zoysiagrasses in a laboratory study, Dallas. TX.

| Cultivar | Textural class[1] | Mean % infection[2] | Mean recovery[3] |
|---|---|---|---|
| Royal | 3 | 15.8 jk | 2.5 def |
| Meyer | 2 | 10.8 k | 3.0 g |

[1]Textural class of zoysiagrass: 1 = short, narrow leaves; 2 = short, wide leaves; 3 = long, narrow leaves; 3 = long, wide leaves.
[2]Mean foliar blighting percentages from a growth chamber inoculation with *Rhizoctonia solani* under heavy disease pressure.
[3]Indicates cultivars recovery from disease and regrowth of leaf tissue in a greenhouse environment, where 3 = best recovery; and 1 = worst recovery.
[4]Means followed by the same letter are not significantly different by Waller-Duncan k-ratio t test (k = 100) (P = 0.05). Only selected means are presented.
Data taken from Metz, 1994.

TABLE 8

Mean number of mite-damaged leaves per zoysiagrass plant in a greenhouse study infested with high populations of zoysiagrass mite (*Eriophyes zoysia*) (18 reps.).

| Cultivar | Leaf texture class | Leaves with symptoms/plant[1,2] (date of evaluation) 3 Apr. 1992 | 24 Apr. 1992 | Mean for combined dates |
|---|---|---|---|---|
| Royal | 3 | 0.2 a | 0.2 a | 0.2 a |
| DALZ8508 | 2 | 0.7 b | 0.6 ab | 0.6 b |
| DALZ8516 | 2 | 1.8 d | 0.3 ab | 1.0 b |
| Emerald | 3 | 1.3 bc | 0.9 b | 1.1 b |
| DALZ8501 | 1 | 1.4 cd | 2.6 c | 2.0 c |
| Crowne | 4 | 5.4 ef | 2.3 c | 3.9 d |
| El Toro | 4 | 5.6 ef | 2.8 c | 4.2 d |
| TC2033 | 2 | 4.4 e | 4.3 d | 4.4 d |
| Palisades | 4 | 7.5 fg | 4.0 cd | 5.8 e |
| CD2031 | 2 | 7.6 gh | 7.9 e | 7.8 f |
| Diamond | 1 | 7.8 gh | 9.4 ef | 8.6 g |
| DALZ8701 | 1 | 9.3 h | 9.4 ef | 9.4 g |
| Cavalier | 3 | 9.1 h | 9.8 ef | 9.5 g |
| Meyer | 2 | 9.9 h | 9.9 ef | 9.9 g |
| Belair | 2 | 10.0 h | 9.9 f | 9.9 g |
| JZ-1 | 4 | 10.0 h | 9.9 f | 10.0 g |

[1]Number of mite infested leaves per plant (>10 = 10). Infested recognized as rolled leaf or hooked leaf tip.
[2]Data transformed using LOG(N+0.5) for analysis. Means in a column followed the same letter are not significantly different by Waller-Duncan k-ratio t test (k = 100) (P = 0.05).
Data taken from Reinert et al., 1993.

TABLE 9

Visual damage evaluation of zoysiagrass, Zoysia spp. genotypes as an indication of resistance to the tropical sod webworm, *Herpetogramma phaeopteralis* in greenhouse tests at Dallas, TX (16 reps.[1]).

| Zoysiagrass Genotype | Visual Damage[1] |
|---|---|
| DALZ8501 | 7.4 a[2] |
| Cavalier | 7.0 a |
| JZ-1 | 6.6 ab |
| CD259-13 | 5.7 bc |
| Crowne | 5.6 bcd |
| Emerald | 5.5 bcd |
| DALZ8508 | 5.3 cd |
| DALZ8701 | 5.0 cd |
| CD2031 | 4.8 cd |
| Royal | 4.6 d |
| TC5018 | 4.5 de |
| Sunburst[2] | 4.5 de |
| Diamond | 3.5 fg |

TABLE 9-continued

Visual damage evaluation of zoysiagrass, Zoysia spp. genotypes as an indication of resistance to the tropical sod webworm, *Herpetogramma phaeopteralis* in greenhouse tests at Dallas, TX (16 reps.[1]).

| Zoysiagrass Genotype | Visual Damage[1] |
|---|---|
| Belair | 3.5 fg |
| El Toro | 3.1 g |
| Palisades[2] | 3.1 g |
| TC2033 | 2.5 g |
| Meyer | 1.4 h |
| DALZ8516 | 1.2 h |

[1]Worm damage ratings 1 to 9; 1 = near complete defoliation, 9 = no damage.
[2]Only 5 replicates were evaluated for Sunburst and Palisades.
[3]Means in a column followed by the same letter are not significantly different by Waller-Duncan k-ratio t test (k = 100) (P = 0.05).
Data taken from Reinert and Engelke, 2001.

TABLE 10

Resistance to tropical sod webworm, *Herpetogramma phaeopteralis*, in zoysiagrass (Zoysia spp.): survival, larval and pupa weight and development time in laboratory no-choice study, Dallas, TX.

| Zoysiagrass genotype | 15-day-old-larvae Alive (%)[1] | Wt (mg)[2] | Pupa Alive (%)[1] | wt (mg)[3] | Days to to pupa[4] |
|---|---|---|---|---|---|
| Cavalier | 60.0 | 7.2 ab[5] | 40.0 | 30.6 h | 31.0 a |
| Korean Common | 53.3 | 6.3 a | 46.7 | 34.9 ef | 29.6 a |
| E1 Toro | 80.0 | 6.9 a | 66.7 | 37.S de | 27.5 b |
| DALZ8501 | 60.0 | 7.5 ab | 60.0 | 32.0 gh | 27.1 bc |
| Palisades | 73.3 | 10.0 abc | 73.3 | 42.1 abc | 25.6 cd |
| JZ-1 | 86.7 | 14.2 abc | 80.0 | 34.0 fg | 24.3 de |
| DALZ8508 | 86.7 | 10.7 abc | 80.0 | 36.8 def | 24.8 de |
| Belair | 86.3 | 15.0 bc | 80.0 | 44.3 a | 23.6 ef |
| Crowne | 80.0 | 15.6 c | 73.3 | 37.3 de | 24.3 de |
| Royal | 86.7 | 15.1 bc | 73.3 | 37.8 de | 24.2 de |
| Emerald | 73.3 | 17.1 c | 40.0 | 41.2 bc | 22.4 f |
| Diamond | 86.3 | 37.5 d | 86.7 | 36.8 ef | 19.7 g |
| Meyer | 93.3 | 36.4 d | 93.3 | 43.4 ab | 19.4 g |
| DALZ8516 | 100 | 41.0d | 100 | 39.8 cd | 19.1 g |

| Zoysiagrass genotype | Adult Alive (%)[1] | Days to adult[4] |
|---|---|---|
| Cavalier | 33.3 | 39.4 a |
| Korean Common | 46.7 | 38.4 ab |
| E1 Toro | 66.7 | 36.7 bc |
| DALZ8501 | 60.0 | 36.2 c |
| Palisades | 66.7 | 35.3 cd |
| JZ-1 | 60.0 | 33.9 de |
| DALZ8508 | 73.3 | 33.4 e |
| Belair | 66.7 | 33.0 ef |
| Crowne | 66.7 | 33.0 ef |
| Royal | 53.3 | 32.9 ef |
| Emerald | 40.0 | 31.3 f |
| Diamond | 86.6 | 28.9 g |
| Meyer | 86.6 | 28.6 g |
| DALZ8516 | 93.3 | 28.5 g |

[1]Mean percentage of larvae alive at 15 day after agg hatch, at pupation and at adult emergence.
[2]Mean weight of surviving larvae after feeding on each genotype for 15 days.
[3]Mean pupa weight for only individuals that pupated (weight taken with 1 day of pupation).
[4]Mean number of days from egg hatch to pupation and adult emergence for larvae on each grass
[5]Means in a column followed by the same letter are not significantly different by Waller-Duncan k-ratio t test (k = 100) (P = 0.05).
Data taken from Reinert and Engelke, 2001.

TABLE 11

Resistance among zoysiagrass cultivars to larval feeding by the hunting billbug (*Sphenophorus venatus vestitus*), Dallas, TX (June–September 2000).

| Cultivar | Species[1] | Plant response: Plant canopy damage % leaf-firing[2] | Plant response: Total plant mass % reduction[3] |
|---|---|---|---|
| Diamond | *Zm* | 6.08 a[4] | 26.29 a |
| Zorro | *Zm* | 9.76 ab | 35.72 ab |
| Cavalier | *Zm* | 27.58 bc | 48.89 bc |
| Royal | *Zm* | 20.95 abc | 53.46 cd |
| Crowne | *Zj* | 40.55 cd | 65.42 de |
| De Anza | *Zj* | 21.90 abc | 68.64 de |
| El Toro | *Zj* | 24.93 abc | 70.24 e |
| Meyer | *Zj* | 44.38 d | 73.90 e |
| Palisades | *Zj* | 45.49 d | 76.10 e |

[1]*Zm* = *Zoysia matrella; Zj* = *Z. japonica.*
[2]Leaf-firing was considered as an above ground symptom expression of the root feeding damage by billbug larvae. Plants were ranked on a scale of 1–9, 1 = severe leaf firing, 9 = no leaf firing. The % damage = [(check − treatment) / check] × 100.
[3]% reduction for cultivar = [(amount in check) − (amount in treatment) / check] × 100.
[4]Means in a column not followed by the same letter are significantly different by LSD test ($P < 0.05$).
Data from Reinert et al., 2002b.

As one of ordinary skill in the art will readily appreciate from the disclosure of the present composition of matter may be utilized according to the present invention. Accordingly, the appended claim is intended to include within its scope such compositions.

REFERENCES

Patents

U.S. Plant Pat. No. 5,845

U.S. Plant Pat. No. 11,570

U.S. Plant Pat. No. 10,778

U.S. Plant Pat. No. 10,636

U.S. Plant Pat. No. 10,187

Publications

Braman, S. K., A. F. Pendley, R. N. Carrow and M. C. Engelke. 1994. Potential resistance in zoysiagrasses to the tawny mole crickets (Orthoptera:Gryllotalpidae) FL Entomol. 77(3): 301–305.

Carrow, R. N. 1991. Zoysiagrass performance, water use, and rooting as affected by traffic and nitrogen. USGA Annu. Rep., Univ. of GA., Griffin, Ga. 5p. 1 table.

Carrow, R. N. 1992. Zoysiagrass performance, water use, and rooting as affected by traffic and nitrogen. USGA Annu. Rep., Univ. of GA, Griffin, Ga. 18 p. 11 tables.

Marcum, K. B., S. J. Anderson and M. C. Engelke. 1998. Salt gland ion secretion: A salinity tolerance mechanism among five zoysiagrass species. Crop. Sci. 38: 806–810.

Metz, S. P., P. F. Colbaugh and M. C. Engelke. 1994a. Rhizoctonia blight on inoculated zoysiagrasses. APS BCT Test Data 9: 158.

Morris, K. 1993. National zoysiagrass test—1991, Progress report 1992. Nat. Turfgrass Eval. Prog. USDA-ARS, Beltsville, Md. NTEP No. 93-4: 32 p.

Morris, K. 1994a. National zoysiagrass test—1991, Progress report 1993. Nat. Turfgrass Eval. Prog. USDA-ARS, Beltsville, Md. NTEP No. 94-5: 54 p.

Morris, K. 1994b. National zoysiagrass test—1991, Progress report 1994. Nat. Turfgrass Eval. Prog. USDA-ARS, Beltsville, Md. NTEP No. 95-8: 66 p.

Morris, K. 1995a. National zoysiagrass test—1991, Progress report 1995. Nat. Turfgrass Eval. Prog. USDA-ARS, Beltsville, Md. NTEP No. 96-6: 54 p.

Morris, K. 1995b. National zoysiagrass test—1991, Final report 1992–95. Nat. Turfgrass Eval. Prog. USDA-ARS, Beltsville, Md. NTEP No. 96–15: 101 p.

Munsell Color Service. 1977. Munsell soil and plant tissue chart. GretagMacbeth, New Windsor, N.Y.

Reinert, J. A. and M. C. Engelke. 2001. Resistance in zoysiagrass, Zoysia spp., to the tropical sod webworm, *Herpetogramma phaeopteralis* Guenee. Int. Turfgrass Soc. Res. J. 9: 798–801.

Reinert, J. A., M. C. Engelke, J. E. McCoy, D. L. Hays, D. Genovesi and J. J. Heitholt. 2002a. Growth characteristics of nine Zoysia cultivars. (unpublished manuscript).

Reinert, J. A., M. C. Engelke, J. E. McCoy, D. L. Hays and J. J. Heitholt. 2002b. Resistance in zoysiagrass (*Zoysia matrella*) to the hunting billbug (*Sphenophorus venatus vestitus*). (unpublished manuscript).

Reinert, J. A., M. C. Engelke, and S. J. Morton. 1993. Zoysiagrass resistance to the zoysiagrass mite, *Eriophyes zoysiae* (Acari: Eriopyidae). Int. Turfgrass Soc. Res. J. 7: 349–352.

White, R. H., M. C. Engelke, S. J. Morton and B. A. Ruemmele. 1993. Irrigation water requirement of zoysiagrass. Int. Turfgrass Soc. Res. J. 7: 587–593.

Yamamoto, I. and M. C. Engelke. 1996. 1996 update of zoysiagrass performance under 90% shade conditions. TX Turfgrass Res.-1996. Consolidated Prog. Rep. TURF-96-11: 65–72.

What is claimed is:

1. A new and distinct cultivar of an asexually reproduced *Zoysia matrella* plant, as herein illustrated and described.

* * * * *